(12) United States Patent
Wenzig et al.

(10) Patent No.: US 7,482,939 B2
(45) Date of Patent: Jan. 27, 2009

(54) ELECTRICAL DROP SURVEILLANCE

(75) Inventors: Peter Wenzig, Munich (DE); Guenter Ziegler, Polling (DE)

(73) Assignee: Roche Molecular Systems, Inc., Pleasanton, CA (US)

( * ) Notice: Subject to any disclaimer, the term of this patent is extended or adjusted under 35 U.S.C. 154(b) by 318 days.

(21) Appl. No.: 11/598,465

(22) Filed: Nov. 13, 2006

(65) Prior Publication Data

US 2007/0109139 A1    May 17, 2007

(30) Foreign Application Priority Data

Nov. 15, 2005   (EP) ................................. 05024898

(51) Int. Cl.
*G08B 21/00* (2006.01)
(52) U.S. Cl. .................. 340/605; 340/612; 340/618; 422/68.1; 436/180; 73/864.11
(58) Field of Classification Search ........... 340/605, 340/620, 612, 618, 619, 623, 686.1; 73/863.03, 73/864, 864.01, 864.11; 422/106, 108, 68.1; 436/180
See application file for complete search history.

(56) References Cited

U.S. PATENT DOCUMENTS

| | | | | |
|---|---|---|---|---|
| 3,754,444 | A | 8/1973 | Spencer et al. ............ 73/423 A |
| 4,166,244 | A * | 8/1979 | Woods et al. ............... 324/693 |
| 4,818,492 | A | 4/1989 | Shimizu .................... 422/100 |
| 5,304,347 | A | 4/1994 | Mann et al. .................. 422/67 |
| 5,503,036 | A | 4/1996 | Nguyen et al. ........... 73/864.34 |
| 5,537,880 | A | 7/1996 | Takeda et al. ............ 73/864.25 |
| 6,551,558 | B1 | 4/2003 | Mann et al. ................. 422/100 |
| 6,555,558 | B2 * | 4/2003 | Chen et al. .................. 514/336 |
| 7,158,039 | B2 * | 1/2007 | Hayashida et al. .......... 340/605 |
| 2001/0014477 | A1 | 8/2001 | Pelc et al. ..................... 436/49 |
| 2001/0049148 | A1 | 12/2001 | Wolk et al. .................. 436/180 |
| 2003/0109052 | A1 | 6/2003 | Eipel et al. .................. 436/149 |
| 2006/0170543 | A1 * | 8/2006 | Schaffer et al. ............. 340/521 |

FOREIGN PATENT DOCUMENTS

| | | |
|---|---|---|
| EP | 0 355 791 B1 | 8/1989 |
| EP | 0 505 004 A2 | 3/1992 |
| EP | 0 164 679 B1 | 7/1992 |
| EP | 0 658 769 A1 | 8/1993 |
| EP | 1 066 532 B1 | 7/2002 |
| EP | 1 316 869 A3 | 1/2005 |
| EP | 05024898.8 | 4/2006 |
| JP | 08334518 | 12/1996 |
| JP | 2003172744 | 6/2003 |
| WO | WO 96/41200 | 12/1996 |
| WO | WO 01/88549 A1 | 11/2001 |

* cited by examiner

*Primary Examiner*—Toan N Pham
(74) *Attorney, Agent, or Firm*—Charles M. Doyle (57) ABSTRACT

The present invention provides a method, an apparatus and a computer program to detect the liquid leakage of a liquid transfer device. In particular, the present invention is directed to a method, an apparatus and a computer program that detects the liquid leakage of a liquid transfer device with electrical means.

19 Claims, 5 Drawing Sheets a)

ELECTRICAL DROP SURVEILLANCE

BACKGROUND OF THE INVENTION

This application claims the benefit of priority under 35 U.S.C. §119 of EP Application 05024898.8 filed Nov. 15, 2005, the contents of which are hereby incorporated by reference.

1. Field of the Invention

The present invention provides a method, an apparatus and a computer program to detect the liquid leakage of a liquid transfer device.

2. Description of Related Art

The increasing degree of automation and parallelization of industrial and scientific processes devotes high demands on the precision and reliability of robotics, especially based on the operational desire to optimize sample volumes and the time-to-result.

For the pharmaceutical industry and diagnostic applications said automation and parallelization concerns the handling of liquids like biological samples or reagents. A prominent example in this respect is the parallelization of PCR amplifications in a microtiter plate format with e.g. 386 or even 1536 individual reactions. To handle such a plurality of assays in a reasonable time frame automation is essential to transport reagents and samples to the microtiter plate.

Every PCR amplification comprises a number of individual preparation steps like lysis of cells, digestion, segregation and purification. Each of the individual preparation steps has to be controlled in order to avoid false overall results. With respect to the handling of liquids, it is important to control the amount of aspirated sample volume, to detect the leakage of the transfer device as well as the completeness of the dispensing process.

Especially the leakage control of the transfer devices is important not only because the amount of transferred liquid must be accurate, but also because a liquid leakage yields the risk of cross-contamination during the transfer process.

In the state of the art the drop surveillance as well as the aspiration/dispensing control is mostly performed by pressure monitoring of the liquid transfer device. WO 96/41200 discloses an automatic pipetting apparatus with leak detection based on a pressure sensor connected to the pipetting system to measure changes of the internal pressure in the pipetting system with time. U.S. Pat. No. 5,503,036 discloses a device and a method for determining whether a sample probe of an automated fluid sample aspiration/dispensing device is obstructed by measuring the pressure within said sample probe. EP 1066532 discloses a method and a device for drawing a biological sample using a manual or automatic suction-discharge device comprising means to detect pressure variations, whereas the pressure monitoring is used for a liquid level detection (LLD) in order to minimize the penetration depth of the device and the corresponding wetting of the outside walls of said device. WO 01/88549 claims a method for determining the quality of an aspiration process comprising the recording of a pressure curve. US 2001/14477 claims a system for dispensing precise quantities of a transfer liquid comprising the step of sensing a pressure change as measure for the volume of dispensed liquid. WO 02/73215 discloses the recording of a state variable during the aspiration and/or dispensing process of a liquid in order to display an evaluation result for the liquid dosing process.

Alternatively, the liquid handling can be supervised by electrical means. US 2001/49148 discloses a method of sampling compounds comprising the step of sensing an electrical signal that is indicative of contact between a solubilizing fluid within a capillary and compounds reversibly immobilized on a surface. JP 2003-172744 discloses a method to place liquid onto the surface of a substrate from the tip of a dropping section, wherein the electrostatic capacity between said substrate and said tip of the dropping section is measured in order to ensure that only droplets generated on the tip of the dropping section are brought into contact with the surface of the substrate.

In the state of the art for liquid handling, electrical means are also used for the liquid level detection (LLD) prior to the aspiration process and there are mainly two different approaches, the resistive LLD (rLLD) and the capacitive LLD (cLLD). Performing the rLLD, simply the electric resistance between the liquid transfer device and e.g. an electrode attached to the outside of the liquid transfer device is measured and the resistance will decrease significantly upon reaching the liquid level (e.g. U.S. Pat. No. 3,754,444). Performing the cLLD, the changes of the electric capacitance between the liquid transfer device and the vessel containing the liquid are monitored using an alternating voltage supply. There are different alternative embodiments of such a setup, e.g. the liquid transfer device itself is constructed as the first electrode and the vessel containing the liquid to be aspirated forms the second electrode. When the liquid transfer device is approaching the liquid level within said vessel, the capacitance will change (EP 164679, EP 355791, U.S. Pat. No. 4,818,492). A more sophisticated approach for a cLLD is disclosed in the EP 555710, wherein both electrodes are part of the liquid transfer device.

SUMMARY OF INVENTION

The present invention discloses a method, an apparatus and a computer program to detect the liquid leakage of a liquid transfer device with electrical means. More particularly, the present invention discloses a method, an apparatus and a computer program for the electrical drop surveillance of liquid transfer devices.

In one aspect, there is provided a method to detect the liquid leakage of a liquid transfer device comprising the steps of:

a) aspirating a liquid from a liquid containing vessel using said liquid transfer device, b) moving said liquid transfer device to a position with a distance d above the liquid level within said vessel and c) measuring an electrical signal between said liquid transfer device and the remaining liquid within said vessel for a measuring time $\Delta t$, wherein a liquid leakage of said liquid transfer device is detected, if said electrical signal measured in step c) changes during said measuring time $\Delta t$.

Within the present invention a liquid transfer device is any device suitable to aspirate a defined amount of liquid at a first location and to dispense said amount of liquid as a whole at one other location or in parts at several other location at some later time. However, if said liquid transfer device looses part of the aspirated liquid with time or if droplets form at said liquid transfer device, this is called a liquid leakage within the scope of this application.

The liquid to be aspirated will be provided in some kind of vessel throughout the present invention, wherein said vessel contains more liquid than necessary for a single aspiration process in most of the cases. Therefore, after the aspiration process, a certain amount of liquid will remain in said vessel. The interface between said remaining liquid within said vessel and the surrounding air is called the liquid level within said vessel. The distance d of the liquid transfer device above said liquid level is defined as the perpendicular distance with respect to the liquid-air interface. Therefore, all positions having a certain distance d to said liquid level represent an imaginary plane above the liquid-air interface with the circumference of the vessel.

Throughout the present invention the liquid leakage of the liquid transfer device is detected using electrical techniques. If an electrical stimulus is applied to some kind of medium, said medium will respond with an electrical signal, wherein said electrical signal is a measure for the electrical properties of the medium. Consequently, if said electrical signal changes during the course of time without changing the electrical stimulus, this is an indication that the electrical properties of the medium changed.

Another aspect of the present invention is a liquid transfer apparatus with electrical liquid leakage detection comprising
 a) an aspiration device to aspirate liquid from a vessel with a liquid transfer device,
 b) a motion device to place said liquid transfer device containing liquid at a position with a distance d above the liquid level within said vessel,
 c) an electrical setup to detect the liquid leakage of said liquid transfer device and
 d) an electronic time clock to control the time $\Delta t$ of liquid leakage detection, wherein said electrical setup is able to detect the liquid leakage of said liquid transfer device by stimulating and measuring an electrical signal between said liquid transfer device and the remaining liquid within said vessel while the liquid transfer device is placed at said distance d above the liquid level within said vessel for said time $\Delta t$.

The phrase "aspiration device" summarizes all devices enabling the aspiration of a controlled amount of liquid from a vessel containing said liquid with a liquid transfer device. In general such an aspiration device will work with low pressure.

A motion device throughout the present invention is a device enabling the motion of the liquid transfer device perpendicular as well as parallel to the liquid level within said vessel.

Throughout the present invention the phrase "electrical device" summarizes all kinds of electrical equipment suitable to apply an electrical stimulus as well as to measure the electrical response of the medium. It is possible to use a single electrical device equipped with both features as well as two separate electrical devices each equipped with one of the features.

The liquid transfer apparatus according to the present invention comprises an electronic time clock to control the time $\Delta t$ of liquid leakage detection. The process of measuring an electrical signal while the liquid transfer device is placed at a distance d above the liquid level within said vessel is called liquid leakage detection throughout the present invention. The time $\Delta t$ of liquid leakage detection is controlled by an electronic time clock, whereas all kinds of electronic time clocks are suitable throughout the present invention as long as they possess a sufficient accuracy.

Yet another aspect of the present invention is a computer program executable by the liquid transfer apparatus according to the present invention to detect the liquid leakage of a liquid transfer device comprising the steps of
 a) defining a permitted liquid leakage rate $V_L$ of said liquid transfer device in terms of a measuring time $\Delta t$ and a distance d of said liquid transfer device above the liquid level within a vessel,
 b) moving the liquid transfer device containing liquid to a position having said predefined distance d above the liquid level within said vessel and
 c) measuring an electrical signal between said liquid transfer device and the liquid within said vessel during said defined measuring time $\Delta t$, wherein a liquid leakage with a liquid leakage rate $V_L$ that is larger than $(4/3 \cdot \pi \cdot (d/2)^3/\Delta t)$ is detected, if said electrical signal changes during said defined measuring time $\Delta t$.

Depending on the time frame necessary to perform the liquid transfer of the present invention as well as on the risk of cross-contaminations, the requirements of the liquid transfer device in terms of leak tightness will vary. Therefore, depending on the application of the liquid transfer device, it is possible to define different permitted liquid leakage rates $V_L$.

DETAILED DESCRIPTION OF THE INVENTION

In one aspect, the present invention provides a method to detect the liquid leakage of a liquid transfer device comprising:
 a) aspirating a liquid from a liquid containing vessel using said liquid transfer device,
 b) moving said liquid transfer device to a position with a distance d above the liquid level within said vessel and
 c) measuring an electrical signal between said liquid transfer device and the remaining liquid within said vessel for a measuring time $\Delta t$, wherein a liquid leakage of said liquid transfer device is detected, if said electrical signal measured in step c) changes during said measuring time $\Delta t$.

Within the present invention, a liquid transfer device is any device suitable to aspirate a defined amount of liquid at a first location and to dispense said amount of liquid as a whole at one other location or in parts at several other location at some later time. The liquid transfer process has to be controlled in order to avoid false results, especially with respect to the detection of any potential leakage of the transfer device. But also the aspiration of sample volume and the completeness of the dispensing process are sources of error for the liquid transfer process.

The leakage control of the liquid transfer devices is important not only because the amount of transferred liquid must be accurate, but also because a liquid leakage yields the risk of cross-contamination during the transfer process. Depending on the design of the experimental setup, the liquid transfer device will cross certain parts of said setup on its way to the dispensing position and the loss of droplets lead to contamination of the setup. Using a setup with e.g. a microtiter plate, the liquid transfer device will cross a certain amount of wells during the transfer process and the loss of droplets may lead to a cross-contamination of samples.

Obviously, the requirements for the liquid transfer device with respect to the contamination by means of liquid leakage are depending on the design of the experimental setup. The acceptable liquid leakage will be smaller for a liquid transfer process that takes a long time and wherein the liquid transfer device crosses a large amount of other vessels.

Throughout the present invention, the liquid leakage of the liquid transfer device is detected using electrical techniques. If an electrical stimulus is applied to some kind of medium, said medium will respond with an electrical signal, wherein said electrical signal is a measure for the properties of the medium. Consequently, if said electrical signal changes during the course of time without changing the electrical stimulus, this is an indication that the electrical properties of the medium changed. For example, if the interspace between two electrodes is filled with air, the electric current in response to an applied electric potential will be negligible, because of the very high electric resistance of air. However, if the interspace is now filled with electrolyte due to the formation of a droplet, the electric current in response to the same applied electric potential will increase significantly due to the smaller electric resistance of the electrolyte.

In comparison to conventional pressure surveillance techniques, the electrical technique of the present invention has the advantage that it is independent of sample density. If pressure measurements are used for the detection of leakage, one has to take into account that the pressure curves are depending on the density of the sample fluid. In other words, the pressure curves of two samples may be different due to density variations and therefore, the detection of leakage can be hindered.

The distribution of sample densities that in case of e.g. blood samples are as much as 10% has no influence on the performance of the electrical drop surveillance technique. The present invention is partly based on the finding that the influence of sample density on leakage detection can be eliminated by implementing an electrical drop surveillance technique.

Note that falling droplets with a diameter smaller than the distance d between the liquid transfer device and the liquid level can not be detected by the present setup. It is necessary that the droplets that form at the tip of the liquid transfer device create a liquid bridge between the liquid transfer device and the liquid level, wherein said liquid bridge can be periodic (periodical formation of droplets) or continuous (permanent flow).

This is another difference compared to pressure surveillance techniques, because here the positioning of the pipette is arbitrary. In other words, for the implementation of the electrical drop surveillance technique of the present invention a thorough understanding of drop formation and pipette positioning is a prerequisite.

Theoretically, it is of course possible to detect also droplet formation without a liquid bridge between the liquid transfer device and the liquid level, if a capacitive measurement is performed that is sensitive enough to detect such small changes of the dielectric surrounding of the liquid transfer device. Therefore, if such a sensitive measurement is performed within the scope of the present invention, the requirement to place the liquid transfer device at a certain distance d above the liquid level within said vessel is no longer necessary.

In one embodiment of the present invention, said aspirating step a) is performed using means to produce low pressure, preferably an air pump or a hose system filled with water.

For the aspiration of liquid, the liquid transfer device has to be partially immersed in the liquid within said vessel. Since the contact of the liquid transfer device with the liquid within the sample bears the risk of contaminations and since the surface of the liquid transfer device will be wetted by the liquid, it is preferred to minimize the immersion depth of the liquid transfer device. Note that it is possible that liquid at the outside of the liquid transfer device may run together and drip off at some later time.

Since the liquid level within the vessel will change during the aspiration, it is necessary to continuously adjust the position of the liquid transfer device. To ensure a sufficient immersion depth of the liquid transfer device during the entire aspiration process, it may be necessary to increase the immersion depth of the liquid transfer device above the required minimal value.

With the liquid transfer device immersed into the liquid within said vessel, the aspiration may be performed by applying low pressure, preferably using an air pump, e.g. a standard syringe. Also preferred is a hose system filled with a system fluid, e.g. a water suction pump.

In another embodiment of the present invention, said liquid transfer device is a pipette tip.

Throughout the present invention, the phrase "pipette tip" summarizes all kinds of hollow bodies having two openings, one for the attachment at said means to produce low pressure and the other for the aspiration of the liquid. It is preferred to use disposable pipette tips in order to avoid sample contaminations and therefore, the attachment between said means to produce low pressure and said pipette tip must be reversible. Since said pipette tips are preferably disposables, it is meaningful to use plastic tips. On the other hand, for certain embodiments it is preferred to provide conductive pipette tips in order to use said pipette tips as electrodes of the electrical setup. It is also preferred to equip said pipette tips with a filter in order to prevent the contamination of said means to produce low pressure.

In one embodiment, said pipette tip has a volume of 0.1 ml to 100 ml, mostly preferred of 1 ml to 10 ml. Said pipette tips have preferably an opening with a diameter of between 0.1 mm and 10 mm.

In yet another embodiment of the present invention, said liquid transfer device in step b) is first moved to a second position with a second distance $d_2$ above said liquid level within said vessel and then, it is moved to approach said liquid again, before said liquid transfer device is placed at said position with a distance d above said liquid level within said vessel.

This embodiment of the present invention can be used, if the liquid level detection can not or only inaccurately be detected during the extraction of the liquid transfer device. In other words, the liquid transfer device is first moved to a distance $d_2$ above said liquid level and than the liquid transfer device is approaching or contacting the liquid level again in order to detect the liquid level. After said liquid level detection, the liquid transfer device is placed at its final distance d (see FIG. 1b).

Moreover, due to the viscosity of liquids, the liquid contact between the liquid transfer device and the liquid within the vessel will not break before a certain distance d' of the liquid transfer device above the liquid level is reached. Therefore, in some embodiments the liquid transfer device has to be moved first to a second position with a second distance $d_2$ that is larger than said distance d', before the liquid transfer device can be placed at its final distance d, if said distance d is smaller than the distance d' (see FIG. 1b).

Figure 1:
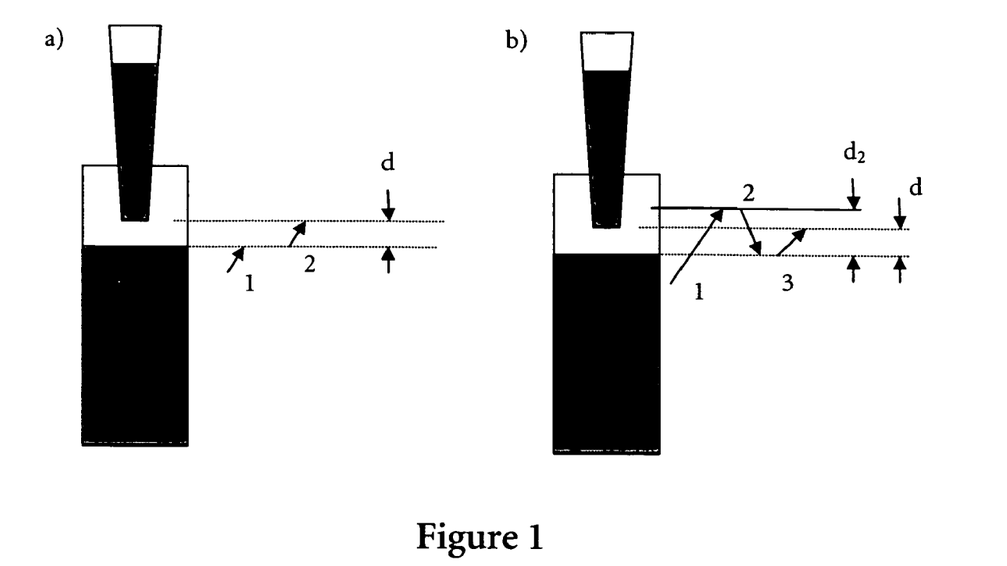
FIG. 1 illustrates a method for positioning of the liquid transfer device above the liquid level in two steps (a) or 3 steps (b).

Note that an accurate positioning of the liquid transfer device at the distance d according to the procedure illustrated in FIG. 1a and FIG. 1b will be hampered, if the liquid leakage rate is too high. In case of a liquid leakage with the formation of droplets already during the positioning the liquid transfer device, the positioning will be imprecise or even impossible.

In another embodiment of the method according to the present invention, said distance d of said liquid transfer device from said liquid level within said vessel is smaller than the diameter of the droplets with volume $V_d$ that may form at said liquid transfer device.

Figure 2:
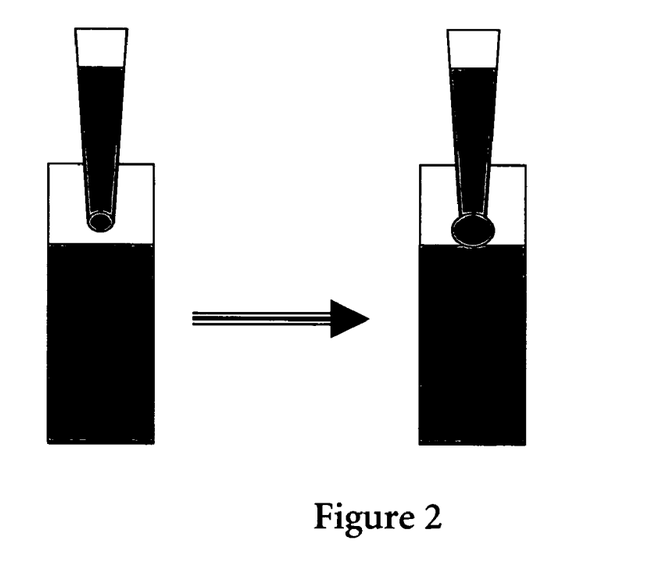
FIG. 2 depicts droplet formation at the tip of the liquid transfer device.

As mentioned before, the electrical liquid leakage detection requires a liquid bridge between the liquid transfer device and the liquid within the vessel in most of the cases (see FIG. 2). If the distance d of said liquid transfer device from said liquid within said vessel is to large, droplets that form at the tip of the liquid transfer device will fall due to gravity prior to the formation of a liquid bridge. Therefore, it is of importance to adjust the distance d with respect to the liquid viscosity and the geometry of the liquid transfer device in order to generate a liquid bridge prior to the tear-off of liquid droplets. Theoretically, it is also possible to detect droplet formation also without a liquid bridge between the liquid transfer device and the liquid level, if a capacitive measurement is performed that is sensitive enough to detect such small changes of the dielectric surrounding of the liquid transfer device.

In yet another embodiment of the method according to the present invention, the volume of the droplets $V_d$ is predefined by the geometry of said liquid transfer device and the surface tension of said liquid.

The surface tension at the liquid-air interface defines the maximum droplet size that may form at a given tip geometry, before gravity induces the droplet tear-off. Without being bound to theory, the volume of the droplets $V_d$ will be larger for fluids having a high surface tension and a low density according to $V_d=(2 \cdot \pi \cdot a \cdot \sigma)/(g \cdot \rho)$, whereas a is the opening diameter of the liquid transfer device, σ the surface tension and the ρ the density of the fluid.

In another embodiment of the method according to the present invention, said droplets have a volume $V_d$ of between 1 μl and 1 ml, preferably between 3 μl and 300 μl.

Using pipette tips with an opening diameter of about 0.7 mm to handle e.g. blood plasma, droplets with a volume of between 4 and 30 μl will form. Using aqueous reagents or a larger opening diameter, the droplet volume will be increased according to the formula mentioned above.

In another embodiment of the method according to the present invention, said distance d of said liquid transfer device from said liquid level within said vessel is between 1 mm and 15 mm, preferably between 2 mm and 4 mm.

Note that the distance d of said liquid transfer device from said liquid level within said vessel must be a bit smaller than the diameter of the droplets for most of the embodiments in order to form a liquid bridge prior to the tear-off of said liquid droplets. If a capacitive measurement is performed that is sensitive enough to detect even droplet formation, said distance d of said liquid transfer device from said liquid level within said vessel can also be larger than the diameter of the droplets.

The electrical signal measured in step c) may be the electric current between said liquid transfer device and said remaining liquid within said vessel.

Figure 3:
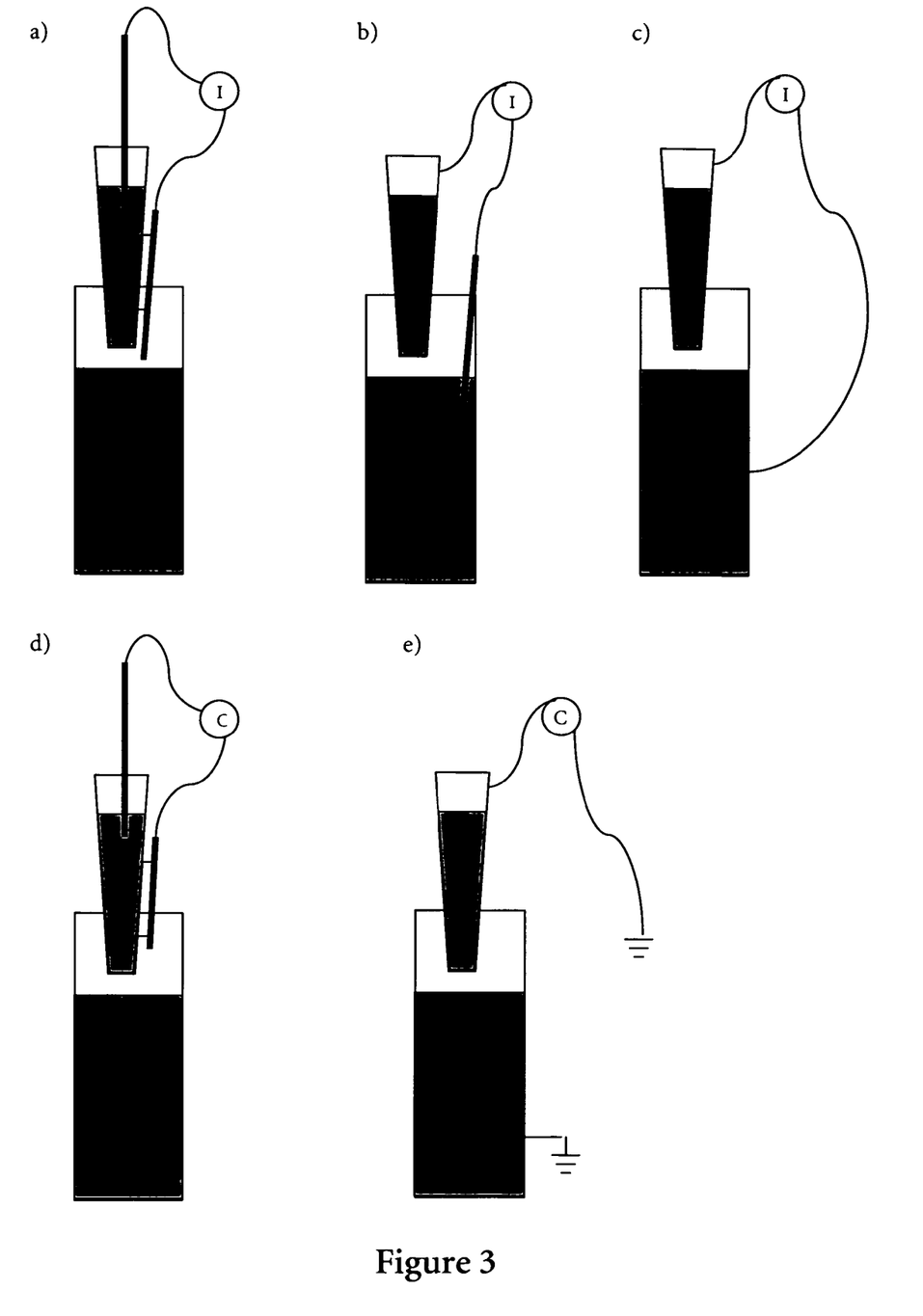
FIG. 3 illustrates electrode setups for measuring the electric current or the electric capacitance, according to embodiments of the invention.

To measure the electric current between said liquid transfer device and said liquid within said vessel an electric potential has to be applied between two electrodes. The liquid transfer device itself may be one of the two desired electrodes (FIGS. 3b and 3c). For this purpose, it is of course necessary to use a conductive liquid transfer device. But it is also possible to use an isolating liquid transfer device and an individual electrode inside the liquid transfer device (FIG. 3a).

With respect to the second electrode, there are at least two possible embodiments. In one embodiment, an individual electrode is immersed into the vessel containing the liquid to be transferred (see FIGS. 3a and 3b). In another embodiment, the vessel containing the liquid to be transferred represents said second electrode itself and therefore needs to be conductive (FIG. 3c).

Another embodiment according to the present invention is a method, wherein said electrical signal measured in step c) is an electric capacitance that depends on the dielectric surrounding of the liquid transfer device.

To measure the electric capacitance between the liquid transfer device and the vessel containing the liquid, an alternating voltage is applied. The electric capacitance C between two electrodes depends on the dielectric constant Å of the connecting material and their distance d according to C~Å/d. Therefore, if the space between the liquid transfer device and said vessel is filled bit by bit with liquid, the electric capacitance will increase due to the higher dielectric constant of liquids (air: Å=1, water: Å=80).

As described with respect to the measurement of an electric current, there are different possible electrode setups also for the capacitive measurement. The liquid transfer device itself can be constructed as the first electrode and the vessel containing the liquid to be aspirated can form the second electrode. A more sophisticated approach for a cLLD is disclosed in the EP 555710, wherein both electrodes are part of the liquid transfer device.

Yet another embodiment of the present invention is a method, wherein said electric capacitance is measured via an electromagnetic field that is generated by said liquid transfer device.

Without being bound to theory, the electromagnetic field emerging from the liquid transfer device depends on the dielectric surrounding. Therefore, the electromagnetic signal measured at another remote electrode will alter, if the dielectric properties between liquid transfer device and said remote electrode changes with time.

The frequency of the electromagnetic field should be rather high in order to increase the voltage difference measured upon changes of the dielectric surrounding, because said voltage difference depends on the ac resistance of the capacitance that is inversely proportional to the ac frequency. On the other hand, at high frequencies problems due to radiation occur and expensive equipment becomes necessary. In one embodiment, a frequency of 50 kHz is applied.

In one embodiment according to the present invention, said liquid transfer device generates the electromagnetic field and measures the electromagnetic signal.

In this embodiment, the liquid transfer device is not only generating the electromagnetic field, but also acts as the second electrode that measures the electromagnetic signal depending on the dielectric surrounding of the liquid transfer device. This electrode setup is illustrated in FIG. 3e), wherein the vessel is grounded. It is apparent that the liquid transfer device has to be conductive in order to realize the setup explained above.

Such a liquid transfer device suitable for the electrode setup as illustrated in FIG. 3e) is e.g. described in U.S. Pat. No. 5,304,347. Here, a liquid transfer needle forms a coaxial electrode arrangement together with two surrounding coaxial electrodes, which are all insulated electrically from the needle and from each other. This application also discloses a suitable detection circuit for such a coaxial electrode arrangement using an a.c. power supply with a relatively high frequency of about 50 kHz.

In one embodiment of the method according to the present invention, said electrical signal is measured for a measuring time $\Delta t$ of at least 1 second, or between 1 and 4 seconds.

The measuring time of the electrical signal depends on the tolerated liquid leakage rate $V_L$. If no electrical signal is detected for a measuring time $\Delta t$, the leakage rate $V_L$ is below $(4/3 \cdot \pi \cdot (d/2)^3/\Delta t)$. In other words, increasing the time without any electrical signal as a requirement to pass a liquid transfer device will reduce the tolerated liquid leakage rate of the device. Moreover, the tolerated liquid leakage rate of the device depends on the transfer time t necessary to move the liquid transfer device from the place of aspiration to another location for dispensing, because during this time no droplet formation may occur.

The method according to the present invention may further comprise the additional steps d) aspirating an amount of air $V_A$,
e) moving said liquid transfer device to a remote location and
f) dispensing said liquid, if the electrical signal measured in step c) does not change during said measuring time $\Delta t$.

In this embodiment of the method according to the present invention, an additional amount of security is gained by aspirating a certain amount of air $V_A$ after the liquid transfer device passed the liquid leakage test of step c). This amount of aspirated air will increase the time until the formation of droplets becomes possible and therefore, reduces the risk of liquid leakage during the movement of said liquid transfer device to a remote location, where all or part of the aspirated liquid should be dispensed.

In another embodiment of the method according to the present invention, said aspiration of air is performed using means to produce low pressure.

As described before, an air pump, e.g. a standard syringe or a hose system filled with a system fluid, e.g. a water suction pump may be used to produce low pressure.

In yet another embodiment of the method according to the present invention, said amount of air $V_A$ is larger than $(V_d/\Delta t) \cdot t$, whereas the movement of the liquid transfer device to said remote location takes a time t.

The amount of aspirated air depends on the liquid leakage rate of the liquid transfer device $V_L = (V_d/\Delta t)$ and the time t necessary to move the liquid transfer device to said remote location for dispensing. If no electrical signal was detected in step c), the liquid leakage is known to be below $V_L$. Therefore, no droplet formation will occur for a time t, if an amount of air $V_A$ larger than $(V_d/\Delta t) \cdot t$ is aspirated.

In another embodiment of the method according to the present invention, said amount of air $V_A$ is at least 3 µl, or between 5-500 µl.

Note that the maximum amount of air that can be aspirated depends on the geometry of the liquid transfer device. If the amount of aspirated air is too large, the air will rise inside of the liquid transfer device in form of a bubble.

With respect to the dispensing step f), said liquid is dispensed by quitting the low pressure applied for the aspiration. Alternatively, the dispensing process may be supported by applying a high pressure.

In a further embodiment of the method according to the present invention, said distance d of said liquid transfer device from said liquid level within said vessel is adjusted based on a liquid level detection (LLD). The LLD may be performed by an electric measurement.

In order to perform the method according to the present invention it is of importance to place the liquid transfer device at a position with a known distance d from said liquid level within said vessel, because only the accurate knowledge of said distance enables the determination of the liquid leakage rate of the liquid transfer device. Therefore, it is necessary to detect the liquid level within said vessel prior to the positioning of the liquid transfer device. The detection of the liquid level within said vessel is called liquid level detection (LLD) throughout the present invention.

It is possible to detect the liquid level within said vessel after the aspiration either during the extraction (FIG. 1a) or by a subsequent approach of the liquid transfer device (FIG. 1b). As mentioned before, the procedure of FIG. 1b can be used, if the liquid level detection can not or only inaccurately be detected during the extraction of the liquid transfer device, e.g. when the liquids tend to form a meniscus before the breakaway of the liquid bridge.

For the method according to the present invention it is preferred that said electric LLD comprises the measurement of the electric current between said liquid transfer device and said liquid within said vessel or the measurement of an electric capacitance that depends on the dielectric surrounding of the liquid transfer device.

As mentioned before, an accurate positioning of the liquid transfer device at a distance d according to the procedures illustrated in FIG. 1a and FIG. 1b will be hampered, if the liquid leakage rate is too high. In case of a liquid leakage with the formation of droplets already during the positioning the liquid transfer device, the positioning will be imprecise or even impossible.

In certain embodiments of the method according to the present invention, said liquid comprises biological samples, nucleotides, enzymes and/or buffer solutions.

The method of the present invention is suitable for all kinds of applications that require liquid handling. Without limiting the scope of the present invention, a reasonable application is the high throughput analysis of biological samples, e.g. blood screening applications. Another example is the preparation of multiple PCR amplifications in a microwell format, where a plurality of reagents like nucleotides, enzymes and buffer solutions have to be prepared.

Another aspect of the present invention is a liquid transfer apparatus with electrical liquid leakage detection comprising
a) an aspiration device to aspirate liquid from a vessel with a liquid transfer device,
b) a motion device to place said liquid transfer device containing liquid at a position with a distance d above the liquid level within said vessel,
c) an electrical setup to detect the liquid leakage of said liquid transfer device and
d) an electronic time clock to control the time $\Delta t$ of liquid leakage detection, wherein said electrical setup is able to detect the liquid leakage of said liquid transfer device by stimulating and measuring an electrical signal between said liquid transfer device and the remaining liquid within said vessel while the liquid transfer device is placed at said distance d above the liquid level within said vessel for said time Δt.

The liquid transfer apparatus according to the present invention is capable of detecting a liquid leakage of a liquid transfer device with electrical means. For the performance of its intended use, the liquid transfer device has to be placed at a certain distance d above the liquid level within said vessel prior to the electrical measurement of said electrical setup, because only the accurate knowledge of said distance enables the determination of the liquid leakage rate of the liquid transfer device.

Moreover, for the accurate determination of the liquid leakage rate of the liquid transfer device, it is also necessary to precisely monitor the time Δt of liquid leakage detection by said electrical setup. Therefore, the liquid transfer apparatus according to the present invention essentially comprises an electronic time clock to control said time Δt of liquid leakage detection.

In one embodiment of the liquid transfer apparatus according to the present invention, said liquid transfer device is a pipette tip.

The meaning of the phrase "pipette tip" was outlined before and it is preferred that said pipette tip is conductive in order to simplify the electrical setup of the liquid transfer apparatus.

In another embodiment of the liquid transfer apparatus according to the present invention, said aspiration device is a device to produce low pressure.

Throughout the present invention said aspiration device to aspirate liquid from a vessel with a liquid transfer device is a device to apply low pressure, preferably an air pump, e.g. a standard syringe or a hose system filled with a system fluid, e.g. a water suction pump.

In another embodiment of the liquid transfer apparatus according to the present invention, said aspiration device is a device to also aspirate air.

To aspirate a certain amount of air after the aspiration of the liquid will reduce the liquid leakage rate of the liquid transfer device and can avoid the droplet formation for the time necessary to move the liquid transfer device to its dispensing position. Note that bubble formation limits the aspiration of air as explained before.

The phrase "electrical mean" summarizes all kinds of device that are able to produce a DC (direct current) or AC (alternating current) stimulus as well as to measure the electric response of the stimulated system.

In yet another embodiment of the liquid transfer apparatus according to the present invention, said electrical setup is able to detect the liquid leakage of said liquid transfer device by stimulating and measuring an electrical signal between said liquid transfer device and the remaining liquid within said vessel, whereas said liquid leakage of said liquid transfer device is detected, if said electrical signal changes during a measuring time Δt.

In still another embodiment of the liquid transfer apparatus according to the present invention, said liquid leakage of said liquid transfer device is detected, if said electrical signal changes during a measuring time Δt.

In other words, the liquid leakage detection of the liquid transfer apparatus according to the present invention is based on changes of the electrical signal between said liquid transfer device and the remaining liquid within the vessel during a measuring time Δt.

As mentioned before, a liquid leakage of the liquid transfer device will alter the dielectric surrounding of said liquid transfer device and can form a conductive liquid bridge to the remaining liquid within said vessel. Monitoring the electric properties of the space between the liquid transfer device and the remaining liquid within said vessel for a certain time Δt, offers the opportunity to detect the presence of a liquid leakage as well as to calculate an estimation of the liquid leakage rate.

In certain embodiments of the liquid transfer apparatus according to the present invention, said electrical setup is able to measure the electric current between said liquid transfer device and said remaining liquid within said vessel or the electric capacitance that depends on the dielectric surrounding of the liquid transfer device.

Performing a DC measurement, it is possible to detect a periodical or a constant liquid bridge between the liquid transfer device and the remaining liquid within said vessel in terms of an abrupt increase of the electric current. Performing an AC measurement, it is possible to measure the electric capacitance between the liquid transfer device and the remaining liquid within said vessel.

There are several different electrode setups to perform the two kinds of measurements possible within the present invention. In certain embodiments, the liquid transfer device itself is one of the two desired electrodes (FIGS. 3b and 3c). For this purpose, it is of course necessary to use a conductive liquid transfer device. But it is also possible to use an isolating liquid transfer device and an individual electrode inside the liquid transfer device (FIGS. 3a and 3d).

In another embodiment of the liquid transfer apparatus according to the present invention, said electrical setup comprises a second electrode to measure the electrical signal between said liquid transfer device and said second electrode.

In another embodiment of the liquid transfer apparatus according to the present invention, said second electrode is the vessel.

With respect to the second electrode, there are mainly two possible embodiments. In one embodiment, an individual electrode is immersed into the vessel containing the liquid to be transferred (see FIG. 3b). In another embodiment, the vessel containing the liquid to be transferred represents said second electrode itself and therefore needs to be conductive (FIG. 3c).

In a further embodiment of the liquid transfer apparatus according to the present invention, said liquid transfer device is able to generate an electromagnetic field and to measure the electromagnetic signal depending on the dielectric surrounding of the liquid transfer device and said vessel is grounded.

If the electric capacitance is measured, the liquid transfer device may be configured in such a way that an electromagnetic field is generated propagating into the dielectric surrounding of the liquid transfer device. In addition, the liquid transfer device may be constructed in such a way that it can measure the electromagnetic signal from the dielectric surrounding, too. In this case the vessel may be grounded and the potential applied between the liquid transfer device and said grounding (FIG. 3e).

In a further embodiment of the liquid transfer apparatus according to the present invention, said distance d of the liquid transfer device from the liquid level within said vessel is smaller than the diameter of the droplets that may form at said liquid transfer device and said diameter of the droplets is predefined by the geometry of said liquid transfer device and the viscosity of said liquid.

The distance d of the liquid transfer device from the liquid level within said vessel depends on the diameter of the droplets that may form at said liquid transfer device. Said diameter itself depends on the surface tension of the used liquid and on the geometry of the opening of the liquid transfer device. These dependencies were already explained in more detail before.

Another embodiment of the liquid transfer apparatus according to the present invention further comprises a liquid level detection (LLD) to adjust said distance d of said liquid transfer device from said liquid level within said vessel. In certain embodiments, said LLD is an electrical LLD.

In certain embodiments of the liquid transfer apparatus according to the present invention, said electrical LLD comprises means to measure the electric current between said liquid transfer device and said liquid within said vessel or an electric capacitance that depends on the dielectric surrounding of the liquid transfer device.

The liquid transfer apparatus can only determine the liquid leakage rate of the liquid transfer device accurately, if the distance d of said liquid transfer device from said liquid level within said vessel is adjusted precisely. Therefore, it is necessary to detect the liquid level within said vessel prior to the positioning of the liquid transfer device and this is preferably done using electrical measurements.

Yet another aspect of the present invention is a computer program executable by the liquid transfer apparatus according to the present invention to detect the liquid leakage of a liquid transfer device comprising
 a) defining a permitted liquid leakage rate $V_L$ of said liquid transfer device in terms of a measuring time $\Delta t$ and a distance d of said liquid transfer device above the liquid level within a vessel,
 b) moving the liquid transfer device containing liquid to a position having said predefined distance d above the liquid level within said vessel and
 c) measuring an electrical signal between said liquid transfer device and the liquid within said vessel during said defined measuring time $\Delta t$, wherein a liquid leakage with a liquid leakage rate $V_L$ that is larger than $(4/3 \cdot \pi \cdot (d/2)^3 / \Delta t)$ is detected, if said electrical signal changes during said defined measuring time $\Delta t$.

Before the computer program according to the present invention can be conducted, it is necessary to define the permitted liquid leakage rate $V_L$ of said liquid transfer device in terms of a measuring time $\Delta t$ and a distance d of said liquid transfer device above the liquid level within said vessel. The permitted liquid leakage rate $V_L$ depends on the time necessary for the liquid transfer device to move to the dispensing location, the required dispensing accuracy and the risk of sample contaminations.

If no change in the electrical signal measured in step c) is detected during the measuring time $\Delta t$, the liquid leakage rate $V_L$ is below $(4/3 \cdot \pi \cdot (d/2)^3 / \Delta t)$. The distance d of said liquid transfer device above the liquid level within a vessel can be defined, if the size of the droplets that may form at the liquid transfer device is identified using information about the geometry of the liquid transfer device and the surface tension of the liquid.

In certain embodiments of the computer program according to the present invention, said electrical signal is the electric current between said liquid transfer device and said remaining liquid within said vessel or an electric capacitance that depends on the dielectric surrounding of the liquid transfer device.

In another embodiment of the computer program according to the present invention, said distance d of the liquid transfer device from the liquid level within said vessel is smaller than the diameter of the droplets with volume $V_d$ that may form at said liquid transfer device and said volume of the droplets $V_d$ is predefined by the geometry of said liquid transfer device and the surface tension of said liquid.

In yet another embodiment of the computer program according to the present invention, said distance d of said liquid transfer device from said liquid level within said vessel is adjusted based on a liquid level detection (LLD). In certain embodiments said LLD is performed by an electrical measurement.

In still another embodiment of the computer program according to the present invention, said LLD is performed by the measurement of the electric current between said liquid transfer device and said liquid within said vessel or by the measurement of an electric capacitance that depends on the dielectric surrounding of the liquid transfer device.

The following example and figures are provided to aid the understanding of the present invention, the true scope of which is set forth in the appended claims. It is understood that modifications can be made in the procedures set forth without departing from the spirit of the invention.

EXAMPLE

The potential-vs-time plots of FIGS. 5-8 were recorded during droplet check measurements of a liquid transfer apparatus according to the present invention.

Figure 4:
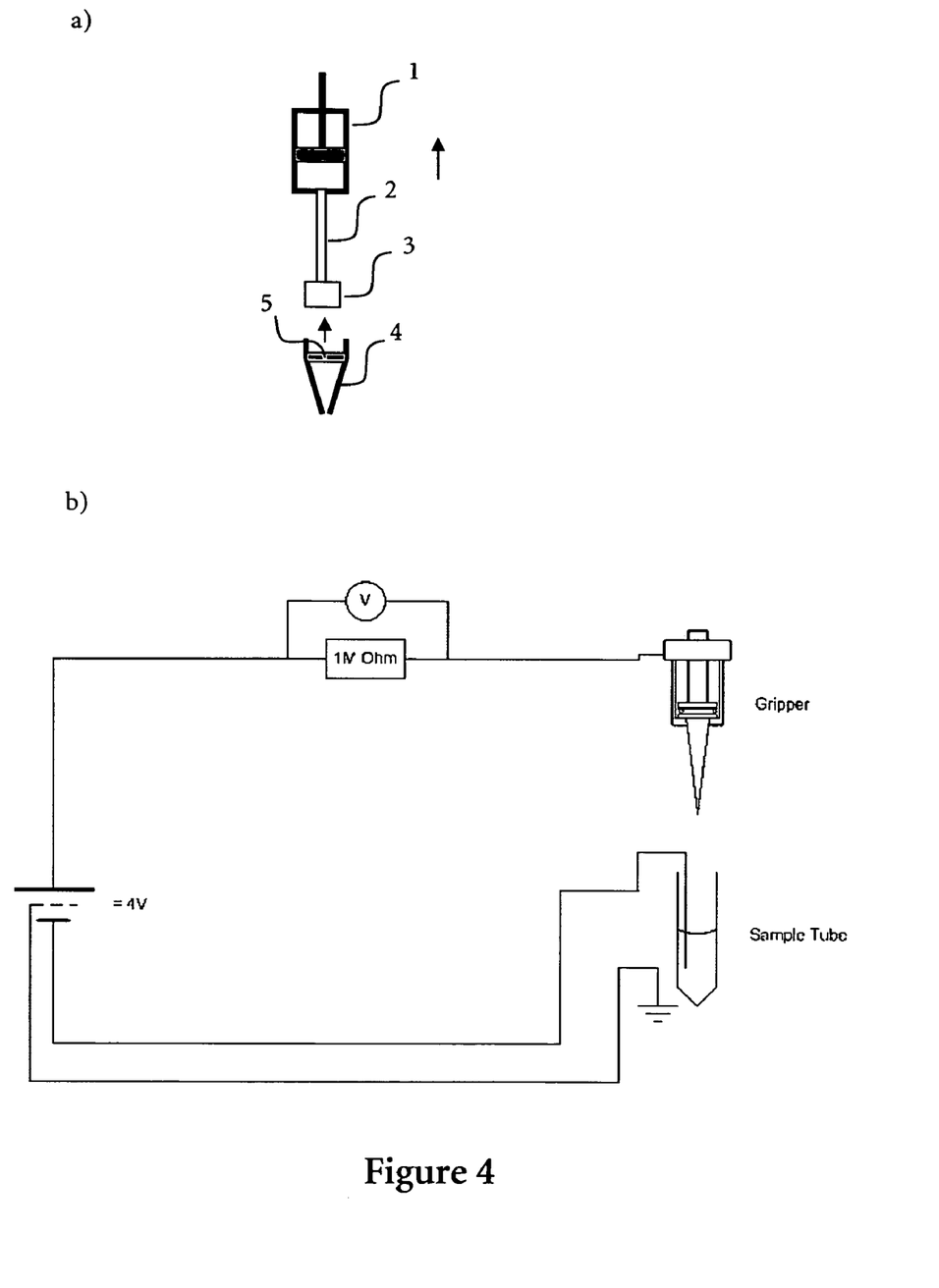
FIG. 4 is a schematic drawing of a disposable together with the tubing system of the gripper (a) and an exemplary electrical setup realizing the resistive droplet check (b), according to embodiments of the invention.

The used liquid transfer apparatus is a home-made prototype equipped with a plunger driven air pump 1 (see FIG. 4a, displacement volume about 5 ml) that was connected via a plastic tubing 2 (see FIG. 4a, inner diameter 1.6 mm) to a gripper unit 3 (see FIG. 4a) that was able to resume disposable plastic tips 4. The complete pipetting system (also called pipettor comprising air pump, connecting tubing and gripper) was mounted on an x,y,z moveable stage, so that the disposable tip could be moved to a vessel in order to aspirated a certain amount of sample volume, checked with respect to droplet loss according to the present invention and transferred to another vessel afterwards that is located at any desirable position accessible by the pipettor.

Throughout the present invention disposable tips were used that had the following characteristics: a maximum aspiration volume of 3.5 ml, equipped with a filter 5 (see FIG. 4a) to avoid decontamination of the gripper (pore size in the range of 30-80 µm), made out of a conductive plastic (major contribution poly propylene), an tip opening diameter of 0.8 mm with a total length of 104 mm.

The vessels containing the sample to be aspirated that were used for this example had the following characteristics: standard 10 ml sample tubes (Becton Dickinson) as typically used for blood screening applications made from conductive poly propylene that have a cylindrical shape with a diameter of 13.3 mm.

The experiments were performed with negative human plasma in EDTA (from internal sources) on a home-made apparatus having the following mechanical functionalities: a pipetting robotics enabling x,y,z movements of the disposable tip, means for the aspiration/dispensing of sample volume with controllable pipetting velocity and a gripper comprising the ability to resume disposables before and discard disposables after aspiration. Moreover, the used apparatus was equipped with means to measure capacitance and resistance in order to perform the electrical drop surveillance according to the present invention.

Using conductive disposables, the liquid transfer apparatus was able to generate an electromagnetic field at the pipette tip and measure the electrical signal depending on the dielectric surrounding, realizing a Capacitive Liquid Level Detection (cLLD) without requiring an additional second electrode.

Nevertheless, the apparatus was equipped with a second electrode (see FIG. 4b, made of copper) immersed in the sample within the vessel in order to enable an additional Resistive Liquid Level Detection (rLLD), wherein the electrical current is measured between said second electrode and the pipette tip.

An exemplary aspiration process with a droplet check measurement using the apparatus according to the present invention with a cLLD and a resistive droplet detection comprises the following steps:

1. Move gripper unit to disposable rack
2. Resume disposable with gripper unit
3. Move gripper with disposable (=pipettor) to sample rack
4. Approach sample with activated cLLD
5. Penetrate 1.5 mm into sample after detection of liquid level
6. Aspirate 850 µl of sample
7. Withdraw pipettor from sample (lift pipettor above sample, no contact to liquid ->cLLD low)
8. Activate rLLD and monitor rLLD signal current
9. Approach sample liquid with cLLD set active
10. When liquid level is found (cLLD high) withdraw pipettor exactly 2 mm from cLLD position
11. Acquire rLLD signal for a period of at least 3 sec to check tightness of disposable tip Note that basically an apparatus according to the present invention does not require two different methods for liquid level detection and it is sufficient to implement either a capacitive or resistive detection. Nevertheless, the implementation of both techniques offers increased flexibility in the design of appropriate measuring procedures.

Figure 5:
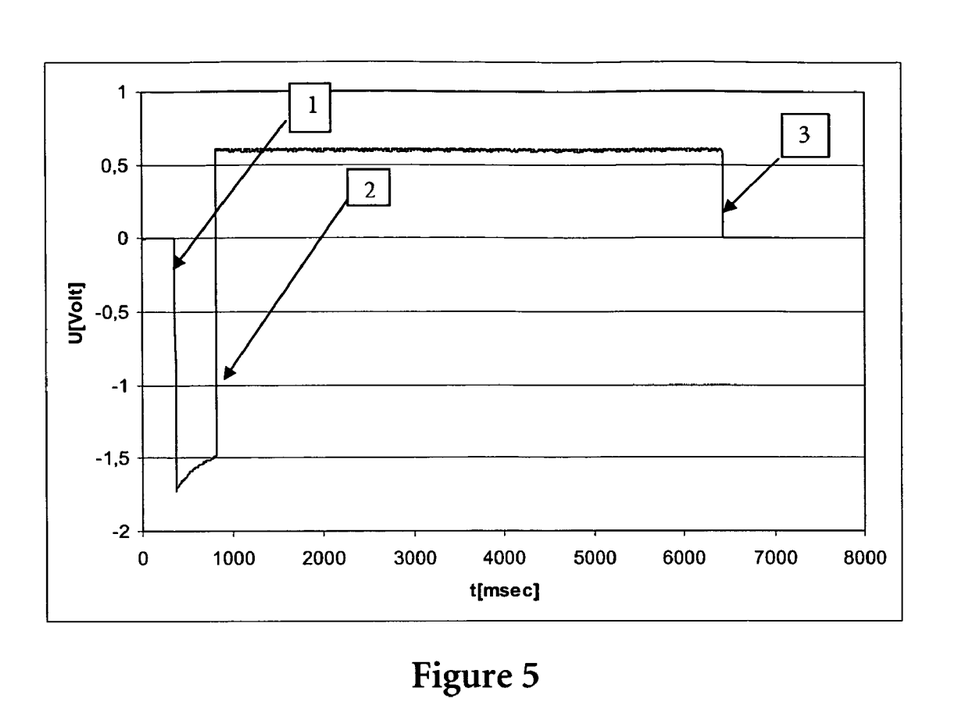
FIG. 5 represents an electrical signal of a positive droplet check.

The experimental data of FIG. 5 shows the rLLD data as obtained during a typical droplet check measurement. The rLLD monitoring starts at step 8 of the process described above, when the pipettor is approaching the liquid surface the second time just after aspiration of the nominal volume. Touching the surface yields a sudden decrease in signal voltage of rLLD signal (indicated by "1" in FIG. 5). After this rLLD detection the pipettor is automatically withdrawn from the surface and positioned at 2 mm above liquid level. During this movement the negative rLLD signal experiences an exponential reduction and at the time, when the physical contact between disposable and sample is disrupted the rLLD signal jumps back to its "non contact level" (indicated by "2" in FIG. 5 at time t=500 msec). During the subsequent hold phase of 5.5 seconds there is no change in the rLLD signals confirming that the gap between the liquid level and disposable tip was maintained, synonymous to a positive result of the droplet check. At time "3" the pipettor is moved to the destination vessel for dispensing.

Figure 6:
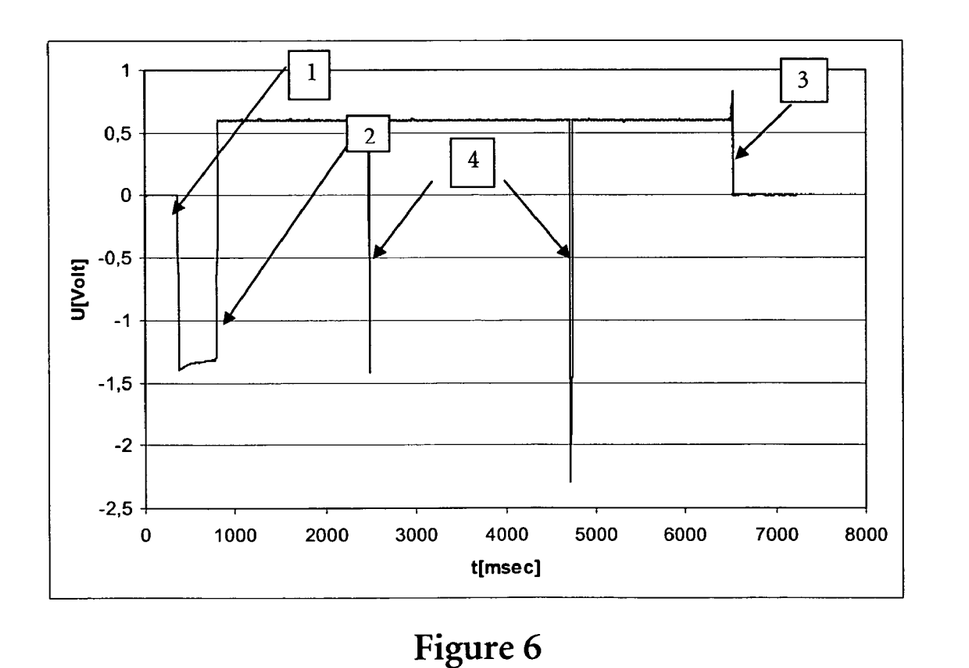
FIG. 6 represents an example of the electrical signal of a droplet check failure.
Figure 7:
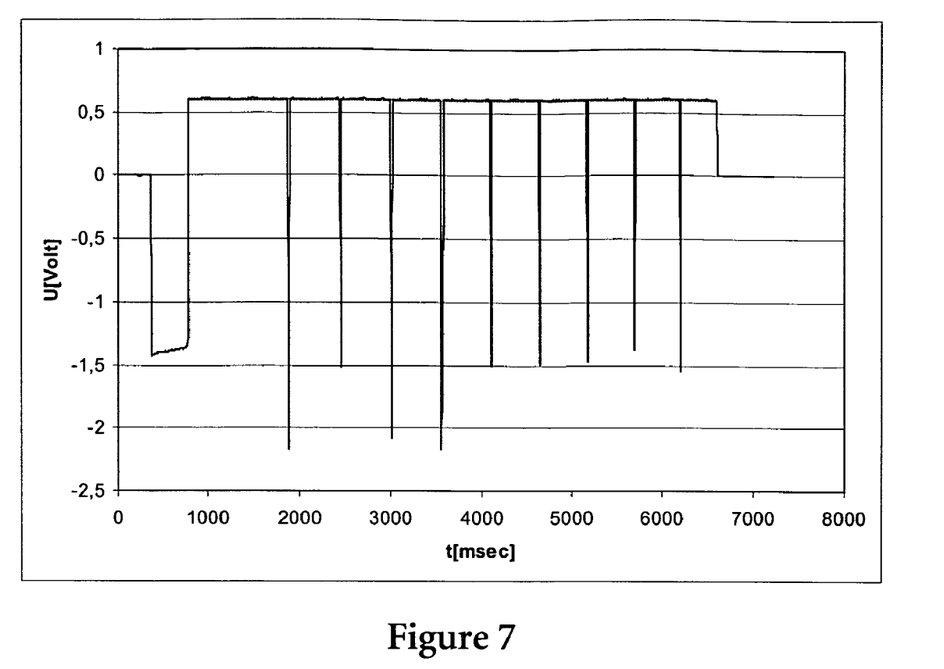
FIG. 7 shows an example of the electrical signal of a droplet check failure.
Figure 8:
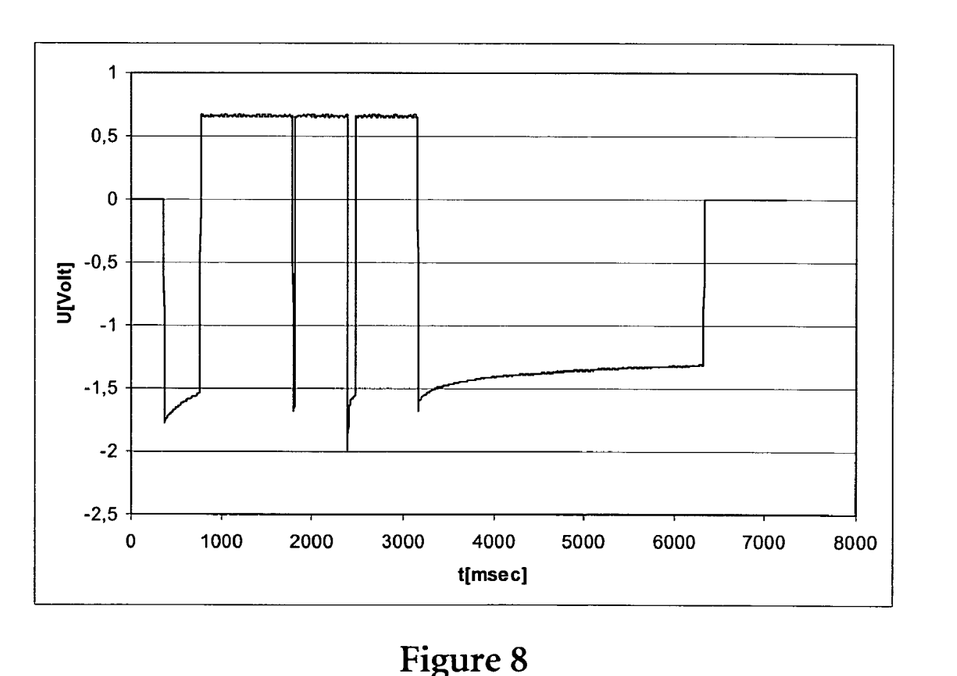
FIG. 8 is an example of the electrical signal of a droplet check failure.

FIG. 6 to 8 show cases of droplet check failure, where the disposable have a liquid leakage rate large enough to be detected with the method according to the present invention.

In FIG. 6 two signal spikes occur in the rLLD signal (indicated by "4") during the droplet check routine in addition two the slopes indicated by "1", "2" and "3" already explained with respect to FIG. 5. Each of these two spikes is indicative of a droplet that formed during the hold period, making a temporary contact between disposable and sample liquid. In between the two droplets the signal switched back to the non contact level as soon as the droplets tear off and there is no longer a contact between the disposable and the sample liquid.

FIG. 7 shows another rLLD signal recorded during a droplet check routine indicating a strongly dripping disposable with the formation of 9 droplets during the same hold time as in FIG. 6.

FIG. 8 shows another kind of droplet check failure detected by recording the rLLD signal. Here, the disposable experience a liquid leakage in form of a constant flow (beginning at around 3000 msec) after the formation of two droplets (indicated by the spikes as explained with respect to FIGS. 6 and 7).

All untight or dripping disposables of this example were prepared by scratching the contact surface between the disposable and disposable handler.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. All publications, patents, patent applications, and/or other documents cited in this application are incorporated by reference in their entirety for all purposes to the same extent as if each individual publication, patent, patent application, and/or other document were individually indicated to be incorporated by reference for all purposes.

What is claimed is:

1. A method to detect liquid leakage from a liquid transfer device, comprising:
   a) aspirating a liquid from a liquid-containing vessel using said liquid transfer device,
   b) moving said liquid transfer device to a first position having a distance d above the liquid level within said vessel, and
   c) measuring an electrical signal between said liquid transfer device and the remaining liquid within said vessel for a measuring time $\Delta t$, wherein a liquid leakage from said liquid transfer device is detected if said electrical signal measured in step c) changes during said measuring time $\Delta t$.

2. The method according to claim 1, wherein, in step b), said liquid transfer device is first moved to a second position with a second distance $d_2$ above said liquid level within said vessel and thereafter, is moved to approach said liquid level, and thereafter, is placed at said first position with a distance d above said liquid level within said vessel.

3. The method according to claim 1, wherein said distance d is smaller than the diameter of one or more droplets with volume $V_d$ that may form at said liquid transfer device, wherein $V_d = (2 \cdot \pi \cdot a \cdot \sigma)/(g \cdot \rho)$ when a is the opening diameter of the liquid transfer device, $\sigma$ is the surface tension, and $\rho$ is the fluid density.

4. The method according to claim 1, wherein said electrical signal measured in step c) is an electric current between said liquid transfer device and said remaining liquid within said vessel.

5. The method according to claim 1, wherein said electrical signal measured in step c) is an electric capacitance.

6. The method according to claim 1, further comprising:
   d) aspirating an amount of air $V_A$,
   e) moving said liquid transfer device away from said liquid-containing vessel, and
   f) dispensing said liquid,
if the electrical signal measured in step c) did not change during said measuring time $\Delta t$.

7. The method according to claim 1, wherein said distance d of said liquid transfer device from said liquid level within said vessel is adjusted based on a liquid level detection (LLD).

8. The method according to claim 7, wherein said LLD is performed by an electric measurement.

9. A liquid transfer apparatus with electrical liquid leakage detection, comprising:
   a) an aspiration device to aspirate liquid from a vessel with a liquid transfer device,
   b) a motion device to place said liquid transfer device containing liquid at a position at a first distance d above the liquid level within said vessel,
   c) an electrical device effective to detect liquid leakage from said liquid transfer device, and
   d) an electronic time clock to measure a time $\Delta t$ of liquid leakage detection, wherein said electrical device is able to detect the liquid leakage of said liquid transfer device by establishing and measuring an electrical signal between said liquid transfer device and said liquid within said vessel while the liquid transfer device is placed at said distance d above the liquid level within said vessel for said time $\Delta t$.

10. The liquid transfer apparatus according to claim 9, wherein said liquid leakage of said liquid transfer device is detected, if said electrical signal changes during said time $\Delta t$.

11. The liquid transfer apparatus according to claim 10, wherein said electrical device is able to measure at least one of an electric current between said liquid transfer device and said liquid within said vessel and a change in electric capacitance.

12. The liquid transfer apparatus according to claim 9, wherein said distance d of the liquid transfer device from the liquid level within said vessel is smaller than the diameter $V_d$ of the droplets that may form at said liquid transfer device, wherein $V_d = (2 \cdot \pi \cdot a \cdot \sigma)/(g \cdot \rho)$ when a is the opening diameter of the liquid transfer device, $\sigma$ is the surface tension, and $\rho$ is the fluid density.

13. The liquid transfer apparatus according to claim 9, further comprising a liquid level detection (LLD) device effective to adjust said distance d of said liquid transfer device from said liquid level within said vessel.

14. The liquid transfer apparatus according to claim 13, wherein said LDD is an electrical LDD.

15. The liquid transfer apparatus of claim 9, further comprising a computer program and a processor, the computer program being effective by the processor to execute the steps of:
   a) defining a permitted liquid leakage rate $V_L$ of said liquid transfer device in terms of a measuring time $\Delta t$ and a distance d of said liquid transfer device above the liquid level within a vessel,
   b) moving the liquid transfer device containing liquid to a position having said predefined distance d above the liquid level within said vessel and
   c) measuring an electrical signal between said liquid transfer device and the liquid within said vessel during said defined measuring time $\Delta t$, wherein a liquid leakage with a liquid leakage rate $V_L$ that is larger than $(4/3 \cdot \pi \cdot (d/2)^3 / \Delta t)$ is detected, if said electrical signal changes during said defined measuring time $\Delta t$.

16. The liquid transfer apparatus according to claim 15, wherein said electrical signal is at least one of an electric current between said liquid transfer device and said liquid within said vessel and a change in electric capacitance.

17. The liquid transfer apparatus according to claim 15, wherein said distance d of the liquid transfer device from the liquid level within said vessel is smaller than the diameter $V_d$ of the droplets that may form at said liquid transfer device, wherein $V_d = (2 \cdot \pi \cdot a \cdot \sigma)/(g \cdot \rho)$ when a is the opening diameter of the liquid transfer device, $\sigma$ is the surface tension, and $\rho$ is the fluid density.

18. The liquid transfer apparatus according to claim 15, further comprising a liquid level detection (LLD) device, the LLD device being effective to adjust said distance d of said liquid transfer device from said liquid level within said vessel.

19. The liquid transfer apparatus according to claim 18, wherein said LLD device adjusts said distance d by an electric measurement.

* * * * *